USOO5646185A

United States Patent [19]
Giaccia et al.

[11] Patent Number: 5,646,185
[45] Date of Patent: Jul. 8, 1997

[54] TUMOR TREATMENT METHOD

[75] Inventors: Amato J. Giaccia, Stanford; Albert C. Koong, Palo Alto, both of Calif.

[73] Assignee: The Board of Trustees of the Leland Stanford Junior University, Stanford, Calif.

[21] Appl. No.: 137,238

[22] Filed: Oct. 14, 1993

[51] Int. Cl.$^6$ .................................... A01N 37/02
[52] U.S. Cl. ........................................ 514/548
[58] Field of Search .............................. 514/548

[56] References Cited

FOREIGN PATENT DOCUMENTS 63250323  4/1987  Japan .

OTHER PUBLICATIONS

Lichtenstein, A, Clin Immunol Immunopathol, (Jun. 1988) 47(3) 296–309 (See Medline 88223894).
Dallegri F et al, Inflammation (Feb. 1991) 15(1) 15–30 (See Medline 91276513).
Stanwell C, et al, Biochem. Pharmacol (May 5, 1993) 45(9) 1753–61 (See Medline 93263889).
Dawson, G., et al., "Regulation of Phospholipase D Activity in a Human oligodendroglioma Cell Line (HOG)," *Journal of Neuroscience Research* 334: 324–330 (1993).
Gali, H.U., et al., "Hydrolyzable tannins: Potent inhibitors of the biochemical markers of skin tumor promotion by thapsigargin," *Proc. Annu. Meet. Am. Assoc. Cancer Res.* 34: p. 180, #1074 (1993).
Koong, A.C., et al., "Activators of Protein Kinase C Selectively Mediate Cellular Cytotoxicity to Hypoxic Cells and Not Aerobic Cells," *Int. J. Radiation Oncology Biol. Phys.* 29(2): 259–265 (1994).
Stanwell, C., et al., "Cytostatic and Cytotoxic Properties of the Marine Product Bistratene A and Analysis of the Role of Protein Kinase C In Its Mode of Action," *Biochemical Pharmacology* 45(9): 1753–1761 (1993).

Tysnes, O–B., and O.D. Laerum, "Differential Effects of 12–0–Tetradecanoyl–13–Phorbol Acetate (TPA) on Growth, Migration and Invasion of a Human Glioma Cell Line," *Anticancer Research* 13: 1325–1330 (1993).
Ganong, B.R., et al., "Specificity and mechanism of protein kinase C activation by sn–1,2–diacylglycerols," *Proc. Natl. Acad. Sci. USA* 83: 1184–1188 (1986).
Giaccia, A.J., et al., "Activation of the heat shock transcription factor by hypoxia in normal and tumor cell lines *in vivo* and *in vitro*," *Int. J. Radiat. Oncol. Biol. Phys.* 23:891–897 (1992).
Giaccia, A., et al., "The use of asymmetric–field inversion gel electrophoresis to predict tumor cell radiosensitivity," *Radiotherapy and Oncology* 231–238 (1992).
Huang, K–P., and F.L. Huang, "How is protein kinase C activated in CNS," *Neurochem. Ing.* 22: 417–433 (1993).
Kim, et al., "Differential expression of protein kinase C & protein in lung cancer cell lines by ionising radiation," *Brit. J. Cancer* 66: 844–849 (1992).

*Primary Examiner*—Paul J. Killos
*Attorney, Agent, or Firm*—Susan T. Evans; Carol A. Stratford; Peter J. Dehlinger

[57] ABSTRACT

Disclosed is a method of treating a solid tumor, where the tumor contains regions of hypoxic cells, either because of poor vascularization in the tumor or because of vasoconstrictive or vaso-occlusive measures brought to bear on the tumor. The method includes administering to a subject, a compound effective to activate protein kinase C activity in the cells of the tumor, via a route effective to direct the compound to such regions of hypoxia in the tumor. Preferred compounds include phorbol esters, diacylglycerols, and thapsigargin. Also disclosed is a vaso-occlusive composition containing a protein kinase C activator, for use in the treatment method.

18 Claims, 7 Drawing Sheets

NFKB:  GGGACTTTCC
       YYY ATT GTT CTC

Fig. 6A

HSE:   CTAGAAGCTTCTAGAAGCTTCTAG
GRE:   GCCGCTTCGAATCGGAAGCCAGCTTGGTGGC
AP-1:  TGA G/C T C/A A

TUMOR TREATMENT METHOD

The invention was supported by a grant from the National Cancer Institute (Grant No. CA03353). The government has certain rights in the invention.

FIELD OF THE INVENTION

The present invention relates to a method of treating a solid tumor, and in particular, to a method involving hypoxic stress as one component and protein kinase C activation as another component.

REFERENCES

Cook, P. F., et al., Biochem. 21: 5794–5799 (1982).

Culver, K., et al., Proc. Natl. Acad. Sci. USA, 88: 3155–3159 (1991).

Farrar, Y. J. K., et al., Biochem. Biophys. Res. Commun. 180: 694–701 (1991).

Farst., et al., NAR 20: 3–26 (1992)

Ganong, B. R., et al., Proc. Nat. Acad. Sci. USA 83: 1184–1188 (1986).

Giaccia, A., et al., Int. J. Radiat. Oncol. Biol. Phys., 23: 891–897 (1992a).

Giaccia, A., et al., Radiotherapy and Oncology, 24: 231–238 (1992b).

Gilman, A. G., et al., *The Pharmacological Basis of Therapeutics*, Eighth Ed., Pergamon Press, New York, (1990).

Huang, K. -P., et al., Neurochem. Ing. 22: 417–433 (1993).

Kim, et al., Brit. J. Cancer, 66: 844–849 (1992).

Kroc, S. et al., Proc. Natl. Acad. Sci. USA 88: 4825–4829 (1991).

Mikisch, G. H. et al., Blood 79: 1087–1093 (1992).

Schreck, et al., Free Rad. Res. Commun. 17: 221–227 (1992).

BACKGROUND OF THE INVENTION

The presence of radioresistant hypoxic cells within solid tumors may contribute to the treatment failure of conventional radiotherapy and some forms of chemotherapy. Cells can survive up to 15 hours of the most severe oxygen deprivation without any change in viability.

It has previously been shown that hypoxic cells undergo changes in cellular metabolism and gene regulation, but little data exists to demonstrate that these changes are responsible for promoting increased survival of those cells in these environmental conditions. In addition, the increased synthesis of some proteins by such cells may not necessarily be harmful, but may be a consequence of cellular organelle damage.

Since poor vascularization is often associated with solid tumors, regions of a tumor containing hypoxic cells are expected. As just noted, these regions may be more resistant to radiotherapy, which is mediated to a certain extent by oxygen-radical damage, and to traditional types of chemotherapy, for example, because of reduced rates of cell division.

It is desirable then to augment these forms of tumor therapy with ones that are able to produce selective cell killing in tumor regions of hypoxic cells. Heretofore, at least one therapy of this type has been proposed—hyperthermic treatment of tumor cells. This approach relies on the reduced circulation in poorly vascularized or vaso-occluded tumor regions (and therefore regions of hypoxic cells) to selectively heat and kill cells when the tumor is heated, for example, by infrared radiation.

The present invention provides another, and generally more versatile, approach to selective killing of regions of hypoxic cells in solid tumors.

SUMMARY OF THE INVENTION

The invention includes, in one aspect, a method of selectively killing cells in a solid tumor in a subject. The method includes administering to the subject, a compound effective to activate protein kinase C (PKC) activity in the cells of the tumor, via a route effective to direct the compound to hypoxic cells in the tumor. This administering is effective to achieve a substantially higher degree of cytotoxicity in the hypoxic cells than in normally oxygenated cells.

The tumor may contain regions of hypoxic cells by virtue of poor vascularization of the tumor, or such regions can be created by inhibiting blood supply to vessels supplying the tumor, for example by administering a vasoconstrictive agent or delivering a vaso-occlusion composition into the vessels. The vaso-occlusion agent may contain the PKC activator compound in releasable form.

Preferred PKC activator compounds include PKC activating phorbol esters, such as 12-O-tetradecanoyl-phorbol-13-acetate and 12-myristate-13-acetate, and phorbol 12, 13 dibutyrate, diacylglycerols, such as 2-acetyl-1-oleylglycerol, and thapsigargin.

The method further includes transfecting cells in the tumor with a vector containing a gene encoding a yeast oxygen-dependent repressor protein, a promoter upstream of the gene effective to ensure high levels of transcription of the gene, an oxygen-dependent repressor sequence, and under the control of this sequence, a minimal promoter and a gene encoding for tumor necrosis factor protein.

Also forming part of the invention is a vaso-occlusive composition for use in treating a solid tumor, by catheter delivery of the composition to vessels feeding the tumor. The composition includes a vaso-occlusion agent effective to form a stable vaso-occlusive mass when injected from a catheter into a vessel, to occlude blood flow in the vessel. Contained within this agent, in a releasable form, is a PKC inhibitor compound.

These and other objects and features of the invention will become more fully apparent when the following detailed description of the invention is read in conjunction with the accompanying drawings.

DETAILED DESCRIPTION OF THE PREFERRED EMBODIMENTS

I. Method of Treatment

In practicing the method of the invention, regions of hypoxic cells in a solid tumor are identified and/or produced by specific vasoconstrictive or vaso-occlusive treatment. These regions are then exposed to a protein kinase C (PKC) activator, to achieve a high level of selective cell necrosis in the hypoxic cells.

A. Localized Hypoxic Regions

1. Solid tumor hypoxic regions

Figure 1:
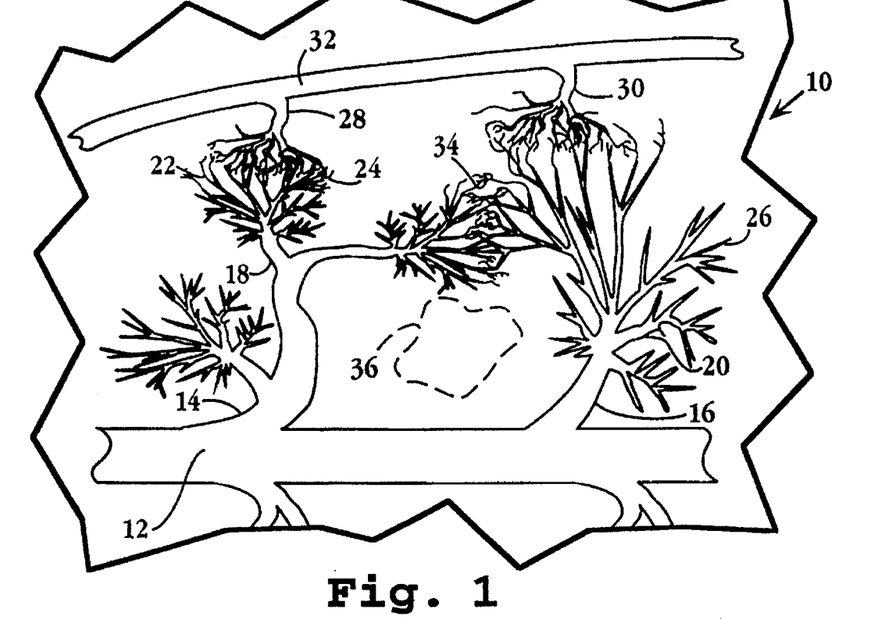
FIG. 1 shows a region of a solid tumor and blood vessels supplying the region.

FIG. 1 shows anatomical features of a solid tumor region 10 vascularized by a network of small blood vessels which branch from arteriole 12. The network, which is shown in schematic form in the figure, includes (a) primary vessels such as vessels 14, 16 branching from arteriole 12; (b) secondary vessels, such as vessels 18, 20 branching from the primary vessels; and (c) tertiary vessels, such as vessels 22, 24, 26, which supply capillary beds (not shown). As indicated in the figure, certain of the capillaries forming capillary beds, are "thoroughfare" capillaries, indicated at 28, 30. Such thoroughfare capillaries provide a connection between arteriole 12 and vein 32. Arteriolar vessel 12, which forms the trunk of the blood-supply network just described has a typical lumen diameter between about 1 to 5 mm. The secondary and tertiary vessels characteristically have diameters ranging between about 10 to 500 microns, and the primary vessels, intermediate sizes, i.e., between about 200 and 1,000 microns.

It is observed from the figure that the secondary and tertiary vessels may contain interconnections, such as at 34, distal to their respective primary vessels. Such interconnections allow blood to be supplied to a smaller vessel by more than one primary vessel and form a collateral blood supply. Usually, the collateral supply becomes an important source of blood for the tissue only after primary vessels are blocked or otherwise damaged.

As illustrated in FIG. 1, tumor region 10 includes an interior hypoxic region 36, which is shown schematically in the figure circumscribed by a dashed line. This region lacks a direct blood supply and is therefore maintained under hypoxic conditions. Nonetheless, blood and nutrients may be supplied to this region by diffusion from the surrounding tissues.

The presence of a hypoxic region in a solid tumor present in a subject can be observed by a number of methods currently known in the art, including nuclear magnetic resonance (NMR) and oxygen electrode $pO_2$ histography. Such methods may be used in the context of the present invention, to identify hypoxic treatment target regions and to guide the practitioner in administering treatment compositions to such regions.

2. Induction of localized hypoxia by vasoconstriction drugs

With continued reference to FIG. 1, it is understood that localized hypoxia can also be induced in a tumor region by any maneuver that results in diminution or cessation of arterial blood flow to tumor 10. Such a maneuver will serve to create or enlarge the hypoxic region 36 present in the tumor.

A number of pharmaceutical vasoconstrictive compounds are known in the art. Preferred agents include alpha adrenergic direct and indirect agonists (for example, norepinephrine, epinephrine, phenylephrine, cocaine). Such compounds, when applied to a specific region, will cause vasoconstriction of veins and arteries in the region, presumably via stimulation of alpha-1 receptors present on the smooth muscle surrounding the vessels. With continued reference to FIG. 1, application of an alpha-adrenergic vasoconstrictive agonist will increase vascular resistance in both arteriole 12 and vein 32 and thereby restrict blood flow to the region. Such restricted blood flow ultimately results in hypoxia of the region normally serviced by the vessels.

Vasoconstrictive agents will preferably be delivered directly to the tumor region, to avoid systemic effects. In accordance with the present invention, it will be understood that a vasoconstrictive agent will be administered to the region for a relatively prolonged period of time; that is, a time that is sufficient to constrict arterioles feeding the tumor region for such a time to produce hypoxia in the region. The period of time required will vary, according to the vascularization of the region and the amount of collateral circulation in the region. It can also be appreciated that sensitivity to vasoconstrictive agents will vary, depending on the physiology of the blood vessels supplying the region. For example, whereas arterioles that supply the skin, abdominal regions, and kidneys are highly sensitive to alpha adrenergic vasoconstrictive agents, arterioles to skeletal muscle are somewhat less sensitive, and cerebral arterioles are much less sensitive to alpha adrenergic stimulation.

From the foregoing, it can be appreciated that the dose of vasoconstrictor agent required depends on the physiology of the region to be treated, as well as the route of administration. In humans, parenteral application of 0.5 ml of a 1/1000 dilution (i.e., 0.1 g/100 ml solution) of epinephrine causes marked systemic vasoconstriction (Gilman). Local application of vasoconstrictor agents may be by direct injection or catheter administration to the tumor region, as described in Subsection C, below.

3. Induction of localized hypoxia by administration of a vaso-occlusive agent

Figure 2A:
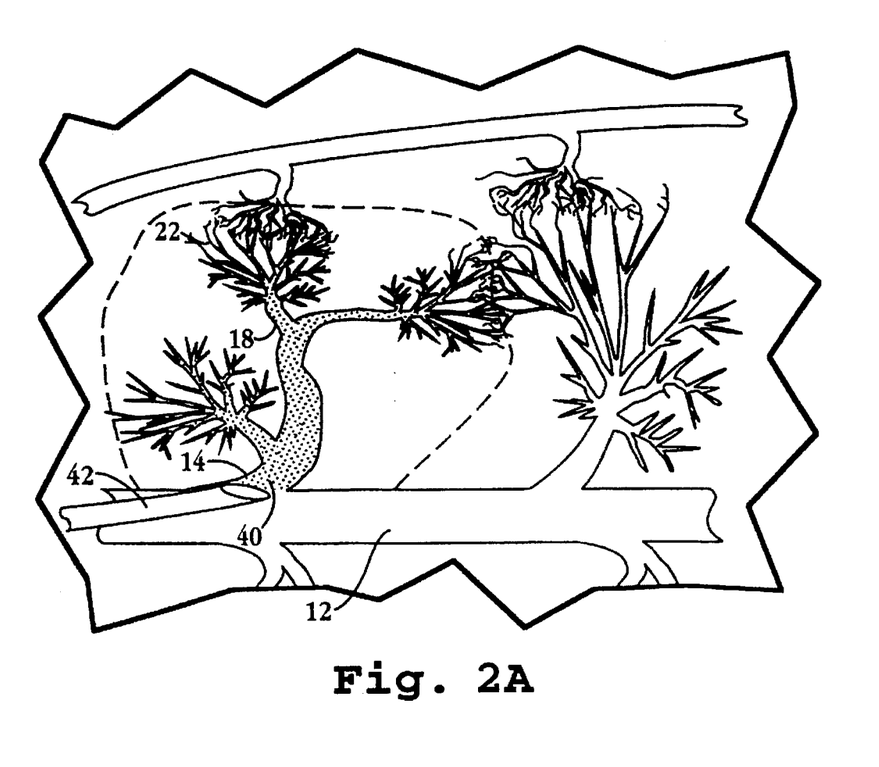
FIG. 2A illustrates the region of solid tumor in FIG. 1., after introduction of a vaso-occlusion agent into the region.

Localized hypoxia may be induced by administering a vaso-occlusive composition to one or more of the primary vessels supplying blood to the tumor. Such a composition will preferably be a biodegradable or biocompatible vaso-occlusive agent, such as a cross-linked collagen, a cross-linked polyethylene glycol, a cross-linked polylactic acid, a cross-linked polyglycolic acid, or the like. FIG. 2A shows a tumor region, as described for FIG. 1, above, where a vaso-occlusive agent 40 has been delivered, via catheter 42 to primary arteriolar vessel 14.

One vaso-occlusive method that is particularly useful in practicing the present invention utilizes a cross-linked fibrillar collagen suspension, prepared as detailed in Example 3. The cross-linked compositions formed by exposing a fibrillar collagen suspension to a glutaraldehyde concentration of 0.0075%. This results in a relatively lightly cross-linked material, which is appropriate when relatively short term vaso-occlusion is desired, as discussed in Subsection C, below.

With continued reference to FIG. 2A, a catheter 42 is inserted into arteriole 12 and is positioned to deliver material into a vessel, such as primary vessel 14, which supplies blood to the tumor region. Once released in the vessel, the vaso-occlusive material is carried by blood flow into the lesser branching arteriolar vessels such as secondary vessel 18 and tertiary vessel 22. As discussed above, such fibers have a size range of about 20–250 microns. Accordingly, the vaso-occlusive composition will be formulated to provide occlusion to such a size range. For example, in accordance with this aspect of the invention, it will be apparent that a cross-linked collagen composition having fibers of this size range will be preferable. For producing a composition having biological persistence of a few months or longer, the material should be cross-linked under conditions that produce moderate-to-heavy cross-linking, such as by treatment with 0.1–1% glutaraldehyde.

Such a collagen vaso-occlusive suspension is formulated for catheter delivery to have a final collagen concentration of between about 0.5 and 15 mg collagen per milliliter, and more preferably between 1 and 5 mg/ml collagen. Such concentrations are suitable for ease of delivery from a small-bore catheter and for ability to be carried by blood flow into small branch blood vessels. The vaso-occlusive composition may include a contrast agent, for fluoroscopic monitoring of distribution to the target site.

Any of a number of catheters known in the art may be used in delivering the vaso-occlusive agent to the tumor site. One preferred catheter is a double balloon catheter, having a pair of balloons which are inflatable independently. With reference to the anatomical configuration illustrated in FIG. 2A, such a catheter can be manipulated to selectively deliver the vaso-occlusive material to the branch vessel of interest. Using a double-balloon apparatus, one balloon will be positioned upstream of vessel 14, while the other balloon is positioned downstream of the vessel. The balloons are inflated, to constrict the vessel adjacent opposite sides of the tumor region. The vaso-occlusive material is then injected under pressure into vessel 14. It can be appreciated that the catheter allows the occlusive material to be injected under pressure, and in a highly localized manner to the tumor region of interest.

In a second general anatomical configuration (not illustrated), the tissue region to be treated is supplied by an arterial vessel which terminates in the tumor region. With this configuration, the occlusive material can be injected into the tissue site selectively using a single-balloon catheter to occlude the upstream side of the injection site, or may be injected under low pressure without vessel occlusion. The volume of vaso-occlusive material that is injected into the tumor region will vary according to (a) the concentration of occlusive material, (b) size of the tumor region, and (c) the extent to which the injected material can be localized at the tumor site. In a typical vaso-occlusion procedure, for occluding a tissue region having a volume between about 5 and 1000 cc, using a cross-linked collagen material at a concentration of about 0.5 to 5 mg protein per milliliter, the total volume of material injected is between about 1 and 200 ml. More generally, the injecting step may be carried out by following the infusion of contrast material into the region, by real-time fluoroscopy, and injecting material until a selected-size region becomes occluded. Adequate occlusion is indicated by progressive slowing of normal flow until complete cessation and ultimately, reversal of direction of normal flow is obtained.

B. PKC Activators

It is a discovery of the present invention that compounds which activate PKC are selectively cytotoxic under hypoxic conditions. PKC is a protein kinase that can be activated by various mechanisms. Several classes of PKC activating compounds have been identified: the phorbol esters; the diacylglycerides,; and certain intracellular calcium releasing agents, such as thapsigargin.

Figure 3:
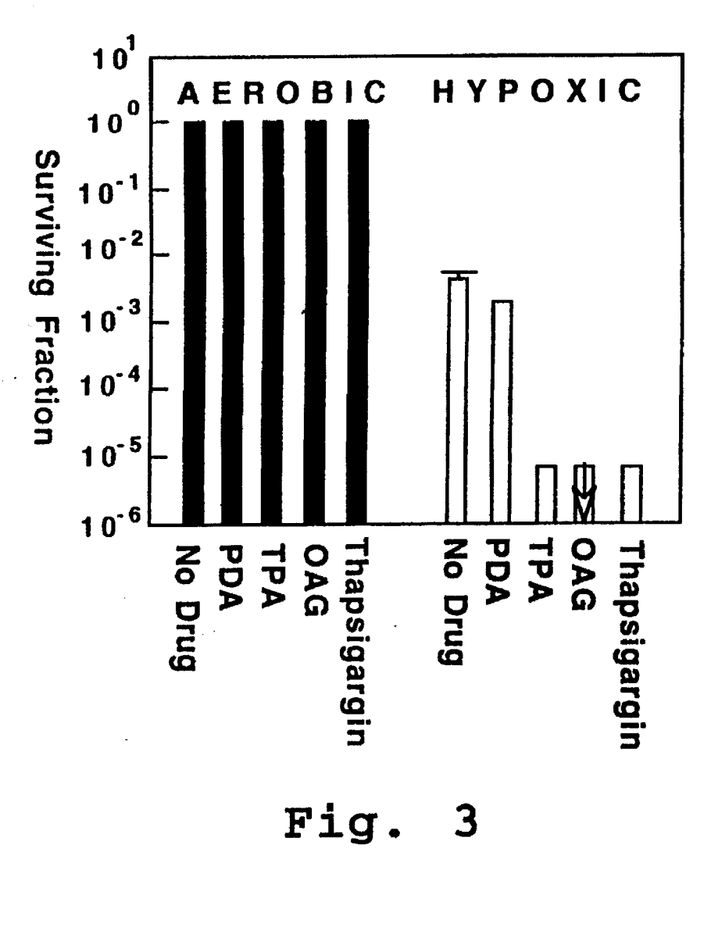
FIG. 3 is a bar graph showing the extent of tumor cell killing under aerobic (solid bars) and hypoxic conditions (open bars) in the presence and absence of PKC activator compounds.

Phorbol esters include a number of related derivative compounds that are known to activate PKC. These compounds are exemplified by 12-O-tetradecanoyl-phorbol-13-acetate (TPA), for purposes of many of the studies carried out in support of the present invention; however, it is appreciated that other PKC activating compounds, including phorbol 12, 13 dibutyrate, 12-myristate-13-acetate (PMA), and the like can be used in the invention. Likewise, diacylglycerols are exemplified by 2-acetyl-1-oleoglycerol (OAG) herein; however, it is appreciated that other diacylglycerol compounds effective to activate PKC can be used in the invention. Structural constraints for diacylglycerol activity in activation of PKC is known in the art and described, for example, in a reference by Ganong, et al., incorporated herein by reference The ability of the compounds to produce selective necrosis in hypoxic tumor cells was demonstrated in A549 human adenocarcinoma cells exposed for varying durations of time to hypoxia, as described in Example 1 below. No measurable effect on survival for the first 10 hours of hypoxic exposure was observed. However, after 15 to 20 hours of hypoxia, there was a reduction in survival of approximately 2.5 log units in survival, as seen in FIG. 3, for no-drug treatment. The survival fraction at 20 hours of hypoxia (0.02% $O_2$) will be used in the following discussion as a baseline for comparing the effects of hypoxic treatment with and without various drugs.

FIG. 3 also shows the effect on tumor cell survival of combined exposure to hypoxic conditions and a PKC activator. The three activators tested are representatives of the three classes of activators discussed above, namely a phorbol ester (TPA), a diacylglyceride (OAG), and thapsigargin. As seen in the figure, none of the PKC activators had an appreciable effect on cell survival in normally oxygenated (aerated) cells. By contrast, each of the three drugs reduced cell survival in hypoxic cells about 1,000 fold in hypoxic cells, relative to the cell survival fraction with hypoxia alone. As a control, cells were also treated with PDA (4α-phorbol-12-13-didecanoate), a phorbol ester which does not bind and activate PKC. As shown, this compound was indistinguishable from no drug treatment on cell survival. Details of cell survival assays are given in Example 1.

C. Administration of PKC Activator to Tumor site

1. Administration of PKC activator compounds

It can be appreciated from the studies described in Subsection B, above, that one important feature of the invention is the discovery that hypoxic cells are susceptible to concentrations of PKC activator that have little or no effect on cells growing under normal aerobic conditions. In the experiments represented in FIG. 3, drug concentrations used approximated the $EC_{50}$ of the drug for activating PKC, in a phorbol ester binding assay or a PKC phosphorylation assay, such as in the assay described in Example 4. The $EC_{50}$ is the concentration of compound that produces half-maximal stimulation of protein kinase C activity in a given assay.

As shown in FIG. 3, at concentrations of 1 µM, PKC activators TPA and OAG selectively killed hypoxic, but not aerobic cells. Likewise, at a concentration of 2 µM, thapsigargin selectively killed hypoxic cells.

In accordance with the present invention, effective cytotoxic dosages of PKC activators are determined from their $EC_{50}$'s for protein kinase C activation, such as in the PKC phosphorylation assay described in Example 4. This concentration is a target mid-range concentration for selective killing of cells in hypoxic tumor regions.

Hypoxic tumor regions to be treated, in accordance with the invention, may be naturally occurring hypoxic regions, as frequently occur in solid tumors. Alternatively, such hypoxic regions can be induced by such methods as localized vasoconstriction or vaso-occlusion, as described in Subsection A, above.

In carrying out the treatment method of the invention, it will be further understood that PKC activators will be delivered to a hypoxic tumor region, and maintained in such a region for a period of time sufficient to observe selective cytotoxicity to hypoxic cells. In one exemplary tumor cell model described herein, it has been observed that a TPA exposure period of 1 hour is sufficient to produce about a $10^{2.5}$-fold decrease in cell survival of hypoxic cells as compared to oxygenated cells. In studies carried out in support of the present invention, it has been observed that certain cells subjected to hypoxic conditions for as little as 2 hours, may be sensitive to PKC activator treatment, as described in the present invention.

a. Parenteral administration

For parenteral administration, a dosage of PKC activator is selected to produce the target mid-range concentration at the tumor site, according to known pharmacokinetic models (Gilman). For example, for TPA, the target tumor concentration is about 0.1–10 micromolar, reflecting a midpoint of 1 µM, the approximate $EC_{50}$ for activation of PKC. Accordingly, a parenteral dose of TPA would be chosen to achieve such a cytotoxic concentration in the bloodstream, or more preferably, in the tumor. It is appreciated that in conjunction with such pharmacokinetic calculations, an appropriate solid animal tumor model can be selected, animals dosed with varying doses of compounds, and the resulting intra-tumor concentrations determined, according to standard analytical methods. From this information, a correlation can be made between blood levels of compound and intra-tumor concentration. Likewise, using the same experimental model, a plasma clearance rate can be determined for the compound of interest. From this rate, a dosing schedule can be determined, according to standard pharmacological principles (Gilman).

b. Intra-tumor injection of PKC activator

For tumor regions that are accessible to hypodermic delivery of agent, it may be desirable to inject PKC activator compounds directly into the hypoxic region. Such a method has the advantage of largely eliminating the need for pharmacokinetic estimations, as required for parenteral injection, and for decreasing the amount of drug required as well as decreasing systemic effects of the agent.

In the case of hypodermic intra-tumor delivery, it will be useful, for accurate delivery of drug, to estimate the hypoxic fraction of the tumor prior to and, if possible, during, delivery of compound. Such estimation can be effected by methods known in the art, including nuclear magnetic resonance (NMR) and oxygen electrode $pO_2$ histography. From this determination, combined with the dimensions of the subject, the practitioner will select a hypodermic syringe having the proper needle length and volume to direct compound to the hypoxic tumor region.

The amount and volume of PKC activator to be administered will mostly depend on the size of the tumor, but may also be affected by tissue metabolism of compound at the site of injection. Generally, the desired volume of used in this mode of administration will be proportional to the volume of the tumor target region, and will not exceed more than about on-half the volume of the tumor. Moreover, the volume as well as the dose of compound administered will be calculated to take into consideration metabolism and excretion of drug, according to standard pharmacological principles. Accordingly, PKC activator compound should be present in a concentration sufficient to provide an effective cytotoxic concentration in the hypoxic tumor region, as described in Subsection A, above.

2. Administration of PKC activators by Catheter

In a preferred embodiment, PKC activators will be delivered to a tumor site by catheter. Generally, standard catheters suitable for delivery of compound may be used in these administration methods; however, in some cases, it may be desirable to use specialized catheters, such as double-balloon catheters, as described in the sections below.

In the catheter delivery methods described, it may also be desirable to include as part of the injectable composition, a radio-opaque contrast agent which allows the material to be monitored fluoroscopically after embolization. Preferred contrast agents include various iodine-containing organic compounds such as diatrizoate meglumine, diatrizoate sodium, ipodamide meglumine, iothalamate meglumine, iothalamate sodium, metrizoic acid, methiodal sodium. Tantalum powder and barium sulfate may be used in the invention. Many of these agents are supplied commercially in sterilized solution or suspension form, at a concentration of between about 20–80 weight percent contrast agent, for use in X-ray fluoroscopy. For use with a vaso-occlusive material in the present invention, the vaso-occlusive material will be suspended in the solution or suspension of contrast agent to produce the desired final concentration. Likewise, the PKC activator compound will be diluted to form the desired final pre-delivery concentration, as described below.

a. Administration of Free drug.

In accordance with the principles discussed in sub-part 1, above, a PKC activator compound is delivered by arterial catheter to a branching arteriole, such as arteriolar vessel 14 in FIG. 1, which supplies blood to the hypoxic tumor region of interest.

In contrast to the parenteral administration paradigm presented in sub-part 1, it will be appreciated that the amount of PKC activator delivered will be an amount sufficient to achieve at least about the target cytotoxic concentration, with reference to the $EC_{50}$ for PKC activation, as described above. Thus, in determining the volume and concentration of PKC activator compound to deliver, the practitioner will take into consideration such factors as the size of the tumor, the blood flow and dilution in the vicinity of the tumor, and the like. In this context, it may be desirable to add to the compound, a radio-opaque pharmaceutical composition, for monitoring of infusion to the appropriate site. It can be appreciated that this mode of administration will be most useful, when the tumor region is supplied by an arterial vessel which terminates in the tumor region. Under these circumstances, the composition can be injected into the tissue site selectively using a single-balloon catheter to occlude the upstream side of the injection site, or may be injected under low pressure without vessel occlusion.

Alternatively, when the anatomical configuration is such that the tumor region is supplied by a continuing artery, such as artery 12 in FIG. 1, it can be appreciated that it will be advantageous to use the double balloon catheter administration method described in Subsection A sub-part 3 above, for selective delivery of compound to the tumor region.

b. Administration of Vaso-occlusive PKC activator Composition.

According to another important aspect of the invention, a tumor region can be treated by administration of a composition containing both a vaso-occlusive agent, as described in Subsection A.3, above, and a protein kinase activator, as described in Sub-part 1.a., above. In conjunction with the foregoing description of vaso-occlusive agents, it will be appreciated that such a composition can be used in the treatment of oxygenated as well as hypoxic tumor regions, since the vaso-occlusive component of the composition will serve to create a hypoxic region, as described below.

The amount and concentration of PKC activator compound present in the vaso-occlusive composition will be essentially as described in the previous section for administration of free drug via catheter. That is, the volume and concentration of PKC activator compound will be determined on the basis of such factors as size of target tumor, blood flow and dilution in the vicinity of the tumor, and the like.

In a preferred embodiment, the vaso-occlusive agent is a collagen-based material, which may be cross-linked. A cross-linked composition that is particularly suitable for use in the present invention is formed according to the methods detailed in Example 3.

Generally, a cross-linked collagen composition will be preferred, since such a cross-linked composition will have the attribute of greater persistence in the biological deposition site. Briefly, a collagen solution is made according to standard methods, such as those described in U.S. Pat. No. 4,140,537, and incorporated herein by reference. The concentration of collagen in the cross-linking reaction is preferably adjusted to 0.1 to 10 mg/ml, and usually between about 1–5 mg/ml. At relatively high collagen concentrations, more interfibrillar cross-linking occurs, at a given concentration of cross-linking agent, leading to larger and more heterogeneous fiber sizes. The larger sizes may be suitable in preparing a cross-linked material for use in occluding large vessels. At lower collagen concentrations, and particularly when the concentration of the cross-linking agent is also low, fiber size may not increase significantly over that of the original collagen suspension. Cross-linked collagen material having smaller fiber sizes is generally preferred in producing vaso-occlusion of relatively small vessels, e.g., having lumen sizes between about 20–250 microns.

The cross-linking agent is preferably an aldehyde, such as formaldehyde, glutaraldehyde, acetaldehyde, glyoxal, pyruvic aldehyde, and dialdehyde starch, which is capable of reacting with and cross-linking free amine groups in collagen. Glutaraldehyde is a preferred cross-linker. The concentration of cross-linking agent is adjusted to produce a selected degree of cross-linking. Using glutaraldehyde as cross-linker, relatively light cross-linking is achieved at concentrations between 0.005% and 0.01%.

Where relatively larger size fibrils are desired (as for use in larger vessels) and/or more persistence is required, cross-linking at concentrations up to 2% glutaraldehyde or greater may be suitable. Degree of cross-linking can be determined, under relatively light cross-linking conditions, by melting point calorimetry. Under relatively heavy conditions, the percentage of lysine residues present in the collagen can be determined, following hydrolysis and amino acid sequencing, according to standard methods. Percentage of lysine will decrease, as percent cross-linking increases.

Generally, it will be understood that in accordance with this aspect of the invention, the characteristics of the vaso-occlusive material present in the composition will be essentially the same as those present in the vaso-occlusive composition described under Subsection A, above. That is, a cross-linked collagen PKC activator suspension is formulated for catheter delivery to have a final collagen concentration of between about 0.5 and 15 mg collagen per milliliter, and more preferably between 1 and 5 mg/ml collagen, to facilitate delivery from a small-bore catheter and for ability to be carried by blood flow into small branch blood vessels. The vaso-occlusive PKC activator composition may also include a contrast agent, for fluoroscopic monitoring of distribution to the target site.

Figure 2B:
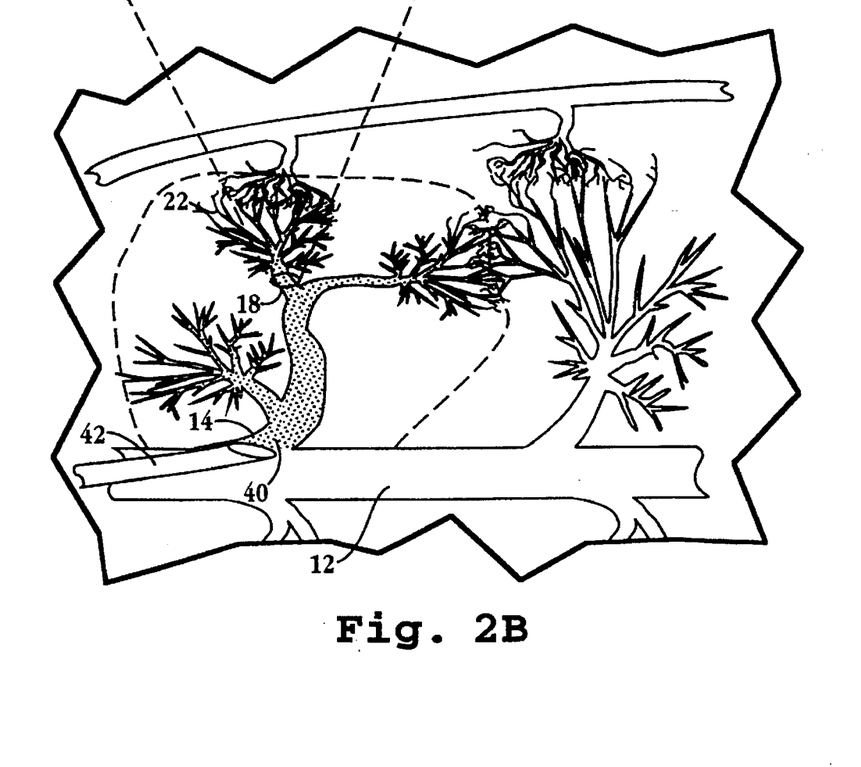
FIG. 2B illustrates the region of solid tumor in FIG. 1., after introduction of PKC activator vaso-occlusion composition into the region.

The PKC activator vaso-occlusive composition is administered to a tumor site, essentially as described in Subsection A, above, for administration of the vaso-occlusive composition alone. With reference to FIG. 2B, a catheter 42 is inserted into arteriole 12 and is positioned to deliver the vaso-occlusive PKC activator into a vessel, such as primary vessel 14, which supplies blood to the tumor region. Once released in the vessel, the composition is carried by blood flow into the lesser branching arteriolar vessels such as secondary vessel 18 and tertiary vessel 22. As discussed above, such vessels have a size range of about 20–250 microns. Accordingly, the vaso-occlusive portion of the composition will be formulated to provide occlusion to such a size range, as described above.

Figure 2C:
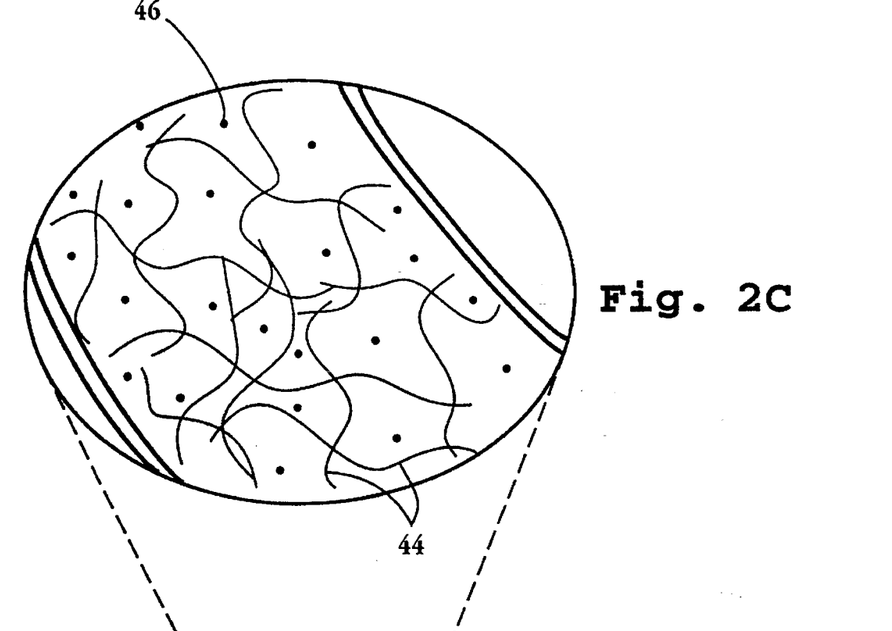
FIG. 2C shows an expansion of a vessel containing PKC activator vaso-occlusion composition.

It will be appreciated, in accordance with the foregoing discussion, that the bulk of the composition will essentially cease to flow, as it encounters vessels, such as vessel 22, having sufficiently small diameter lumen size. The expansion of the vessel shown in FIG. 2C shows the presence in vasculature of cross-linked collagen fibrils 44 and PKC activator compound 46 in the free spaces between the fibrils. In contrast to the collagen occlusion material, PKC activator compound present in the composition is free to passage from the vessels to the surrounding tissue. Once in the tissue, the compound will pass by diffusion into the hypoxic treatment zone, schematically delineated in FIG. 2B by the dashed line circumscribing the occluded vessel region. In accordance with the invention, the presence of PKC activator compound in the tissue region will be effective to selectively kill hypoxic tumor cells, under the hypoxic conditions provided by the vaso-occlusion.

D. Introduction of Hypoxia-sensitive elements into Tumor Cells

Known in the medical literature are manipulations for introducing specific genetic material into cells. Such "gene therapy" has been particularly successful in treatment of blood lymphocytes (Culver).

Figure 5:
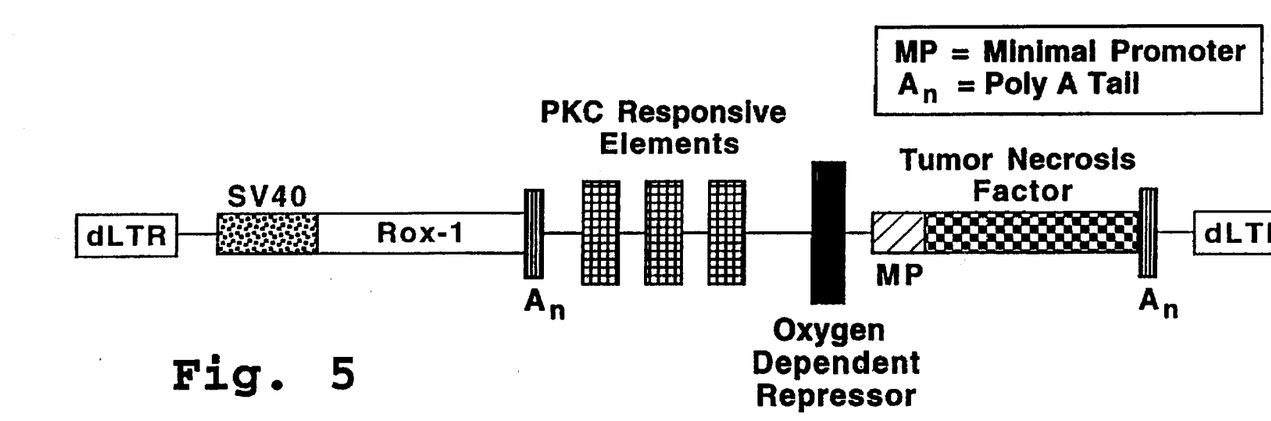
FIG. 5 shows a portion of a vector used for gene therapy in conjunction with the present invention.
Figure 6A:
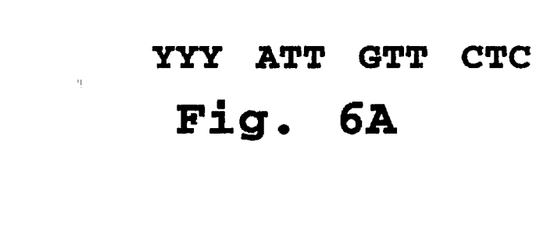
FIG. 6A shows the sequence of the yeast oxygen dependent repressor (SEQ ID NO: 1)

FIG. 5 shows a partial vector construction that is particularly useful in the present invention, for selectively inducing, under hypoxic conditions, synthesis of a cytotoxic peptide product, exemplified by in the vector illustrated as Tumor Necrosis Factor (TNF). Shown in the figure is a construct which includes ROX-1, a yeast gene that encodes for a repressor which binds specifically to an Oxygen-dependent repressor (ODR) in selected cells. This repressor element is placed under the control of an SV40 promoter to ensure high levels of synthesis. An exemplary ODR sequence is shown as SEQ ID NO: 1 in FIG. 6A. With continued reference to FIG. 5, it can be seen that the ODR is upstream of and controls transcription of the gene for a cytotoxic protein, Tumor Necrosis Factor (TNF). Also upstream of and controlling the TNF gene is a PKC Responsive Element.

As noted above, the combination of elements shown in the vector insert of FIG. 5 allows a high constitutive rate of transcription of the ROX-1 repressor. Under normal aerobic conditions, the repressor protein will be synthesized and will remain bound to the ODR. Under such conditions no transcription of the TNF gene will occur. Under conditions of hypoxia or low oxygen stress, the ROX-1 repressor will not be able to bind to the ODR. Under these circumstances, transcription of the TNF gene will be permitted, and the resulting TNF will be cytotoxic to such cells.

Figure 6B:
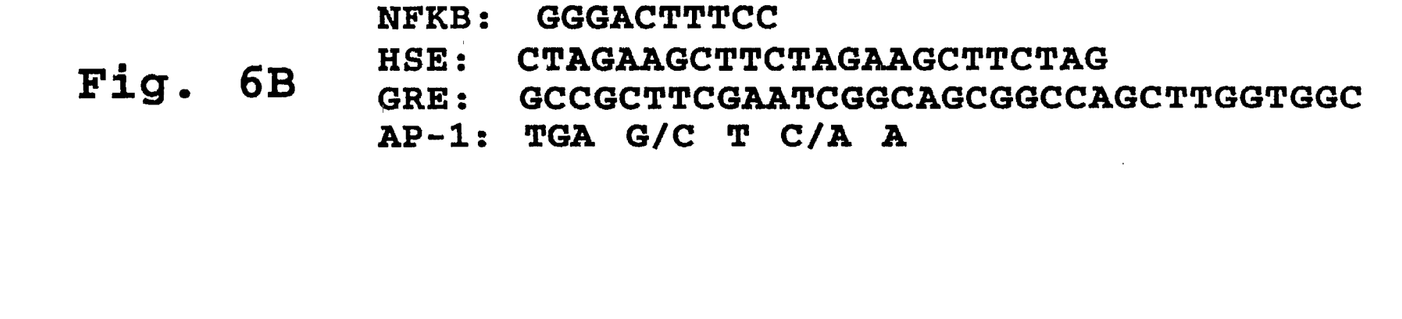
FIG. 6B shows sequences of PKC responsive elements NFKB (SEQ ID NO: 2), HSE (SEQ ID NO: 3), GRE SEQ ID NO: 4 and AP1-1 (SEQ ID NO: 5) suitable for inclusion in the vector of FIG. 5.

As a further means of effecting selectivity, a PKC Responsive element may be positioned in the vector upstream of the TNF gene. Exemplary PKC Responsive elements that may be included in the vector include Glucose-related Core element, Nuclear Factor-kappa B (NFKB), Heat shock transcription factor (HSE), GRE and AP-1. Sequences for these exemplary elements are shown in FIG. 6B. Inclusion of one or more such elements in the vector with the ROX-1 gene will provide heightened sensitivity to hypoxia and/or PKC activators. The illustrative construction of FIG. 5 includes three such elements. Although the vector as illustrated in FIG. 5 shows control over TNF transcription by both ROX-1/ODR and PKC responsive elements, it is appreciated that in the context of the present invention, the Rox-1/ODR combination alone will provide the desired hypoxia-dependent control over TNF production.

It can be appreciated that the current invention will include gene therapy with the vector illustrated in FIG. 5 as an insertion gene. In practicing the invention, such a sequence is incorporated, according to standard methods, into a mammalian vector suitable for transfecting mammalian cells in vivo, such as an Adeno-associated virus, a modified Vaccinia virus, an Epstein Barr virus, or the like. Generally preferred vectors will be retroviruses.

Methods for introducing genes into mammalian cells are known in the art (Culver, Mikisch). The vector is introduced to the subject, preferably by injection directed to the tumor, as described in subsection C.1.b., above. It is appreciated that the vector may be introduced into target cells as well as non-target cells in the vicinity of the tumor, when the vector is directly injected into the tumor, and that more general dissemination of the vector can be expected, when the vector is administered by less direct means, such as by parenteral injection.

Selectivity for tumor cells is achieved by rendering the target tumor hypoxic, as by any of the means described in Section I.A., above. Under hypoxic conditions, as described herein, production of TNF will be de-repressed in such tumor cells, resulting in cytotoxicity. Moreover, when the vector also contains a PKC responsive element, as illustrated in FIG. 5, it will be appreciated that such cells will become exceptionally sensitive to PKC activator compounds, as described in Section I, above.

From the foregoing, various advantages of the treatment methods of the invention can be appreciated. For example, it can be seen that such hypoxia will serve as a complement to other tumor treatment therapies to which hypoxic cells may be resistant. Moreover, the hypoxia-related treatment methods target areas of poor vascularization, resulting in hypoxia, in solid tumors. It can also be appreciated from the foregoing that the treatment method of the invention has the advantage of selectivity for target tumor regions over normal, healthy cells. That is, at the concentrations used, PKC activator compounds that are cytotoxic in such hypoxic cells have relatively little effect on normally oxygenated cells.

II. Mechanism of Tumor-Cell Killing

The studies reported in this section are aimed at determining the mechanism by which PKC activator compounds selectively enhance cell killing in hypoxic tumor cells. The studies examined (i) the dependence of cell killing on PKC activation in hypoxic cells, (ii) the relationship between cell killing and DNA degradation in treated cells, and (iii) the role of phospholipase activation in cell necrosis.

A. Dependence on PKC Activation in Hypoxic Cells

Figure 4:
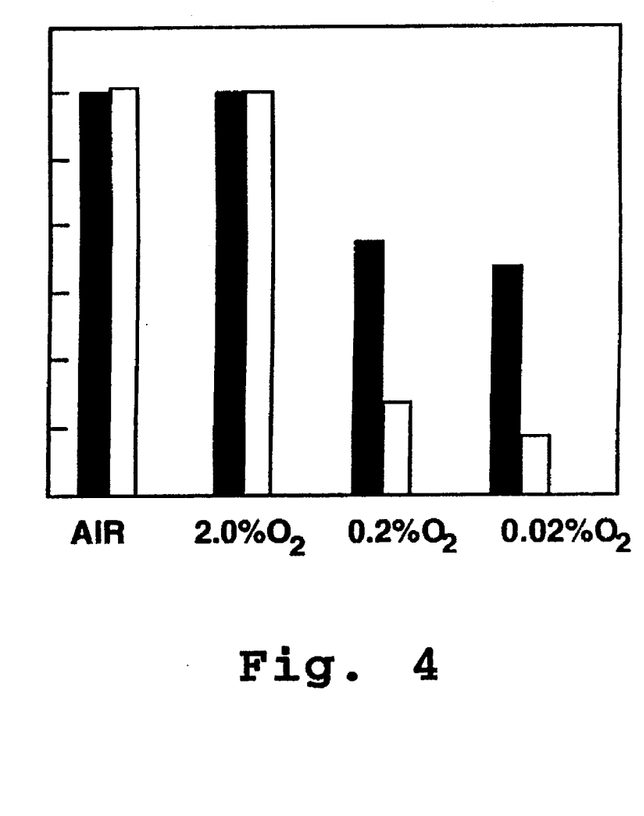
FIG. 4 is a bar graph showing effects of various levels of hypoxia on cytotoxicity in the absence (open bars) or presence (closed bars) of PKC activator.

FIG. 4 demonstrates the effect of varying the level of oxygen on cell survival. The cells were treated as described in Example 1. Briefly, cells were subjected to 1, 3, or 5 rounds of evacuation/N2 gassing, as described in Example 1, to produce $O_2$ levels of about 2%, 0.2% and 0.02% oxygen, respectively.

The cells were then incubated under the selected hypoxic condition for 19 hours. The extent of killing was dependent on both the degree of hypoxia and the time of exposure to hypoxic conditions. In experiments in which cells were exposed to varying periods of 0.02% oxygen, a 50-fold decrease in cell survival was observed in the period 10–15 hours of hypoxia.

The effect of PKC activator compounds on aerobic and hypoxic tumor cells has been described above. The data in FIG. 4 show that in all cases where a PKC activator was employed, at least about a 100 fold reduction of cell viability was seen in hypoxic cell populations. Little or no reduction in cell survival was seen in normally oxygenated cells treated with the same compounds.

Figure 7A:
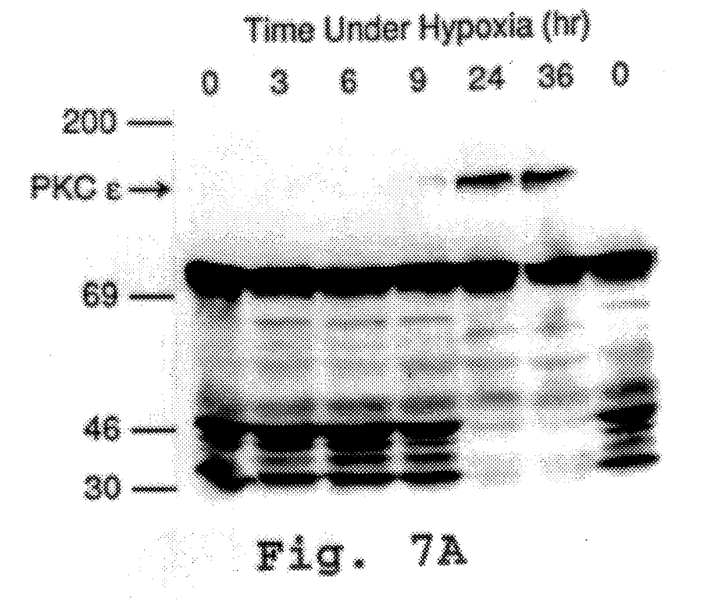
FIGS. 7A and 7B are Western blots showing the induction of PKC in tumor cells with increasing time under hypoxia (7A) and in hypoxic tumor cells in the presence and absence of TPA, a PKC activator (7B)

Western blotting methods, as detailed in Example 2, were used to validate that the treatment method of the invention increases levels of PKC. FIG. 7A is a Western blot which shows that the epsilon isoform of PKC, the predominant PKC isoform in this cell, accumulates in a time dependent manner when exposed to 0.02% oxygen. Little accumulation is seen before 9 hours of hypoxic exposure. However, by 24 hours, PKC is increased approximately 10-fold, demonstrating that hypoxic treatment itself causes PKC accumulation.

Figure 7B:
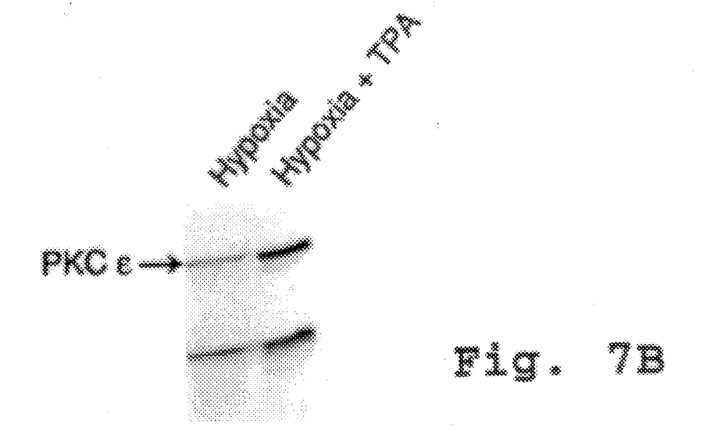

Next, as illustrated in FIG. 7B, a one hour exposure of hypoxic cells to TPA shows an increase in PKC levels 5-fold over that of hypoxia alone. Although there is an induction of PKC in cells treated with only hypoxia, there is an even greater induction of PKC in cells treated with TPA following 19 hours of hypoxia. PDA, the non-PKC binding phorbol ester, has no effect on steady state levels of PKC (data not shown).

B. DNA Degradation

The mechanism of cell death by hypoxia appears to be necrosis rather than apoptosis. Using pulsed-field gel electrophoresis, a steady increase in DNA degradation as a function of time under hypoxia may be found. The methods followed those given in Example 2. The pattern of DNA degradation (not shown) is not one that is characteristic of apoptosis. The DNA was not fragmented into distinct nucleosome ladders, which is one of the hallmark characteristics of apoptosis; rather, it separated as a smear which is indicative of death by necrosis. Of particular interest is the fact that addition of TPA to hypoxia treated cells does not increase DNA fragmentation over that found with hypoxia treatment alone.

C. Effect on Phospholipase Activity

Figure 8:
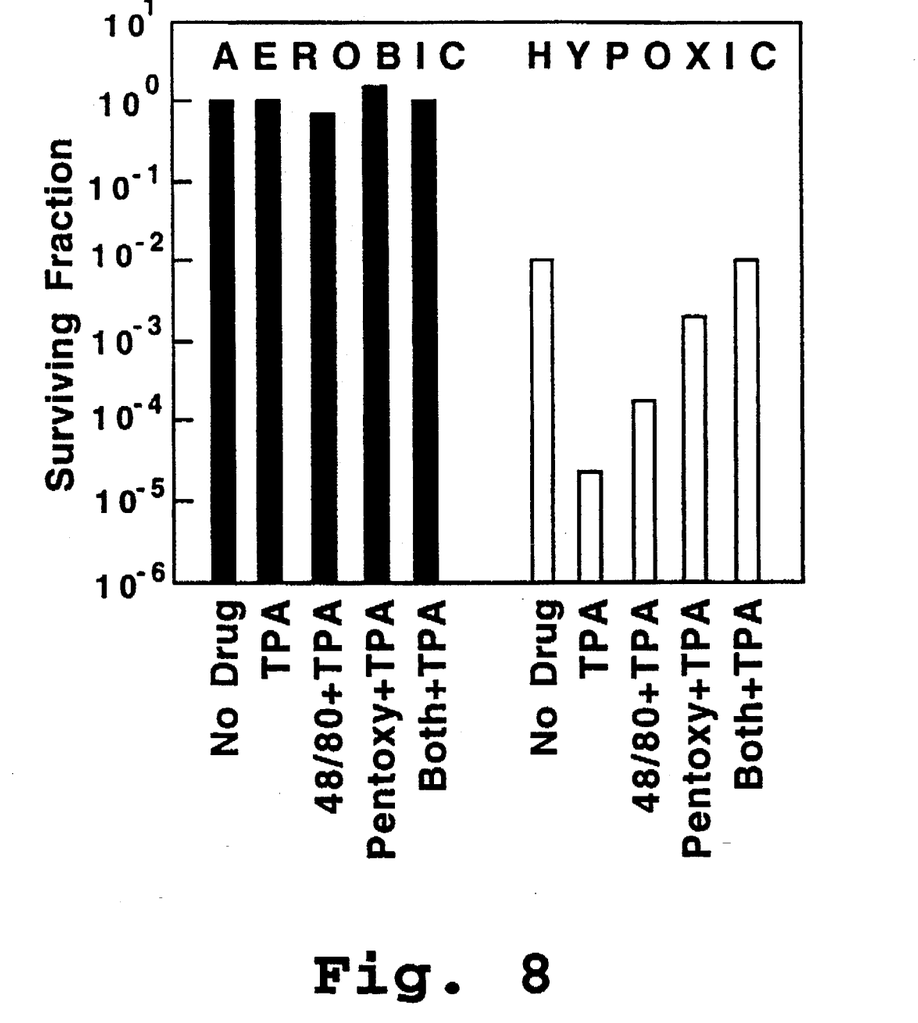
FIG. 8 is a bar graph showing the effect of phospholipase inhibitors in tumor cells treated with a PKC activator under aerobic and hypoxic conditions.

PKC mediated hypoxic cell killing appears to be a membrane event rather than a DNA event. To determine whether PKC was activating phospholipases to increase phospholipid breakdown of the membrane, inhibitors for phospholipase $A_2$ and C were examined for their ability to protect against TPA mediated hypoxic cell killing is assessed. FIG. 8 shows the survival of aerobic cells and hypoxic cells treated with TPA alone or in combination with compound 48/80, and pentoxyfylline. Compound 48/80 which inhibits phosphatidylinositol-specific phospholipase C and $Ca^{2+}$-dependent phospholipase $A_2$, provide approximately 10-fold protection when added prior to TPA treatment. A second phospholipase inhibitor, pentoxyfylline, affords a 100-fold (2 log units) increase in survival. When both inhibitors are added together with TPA, cell killing is completely eliminated.

Figure 9:
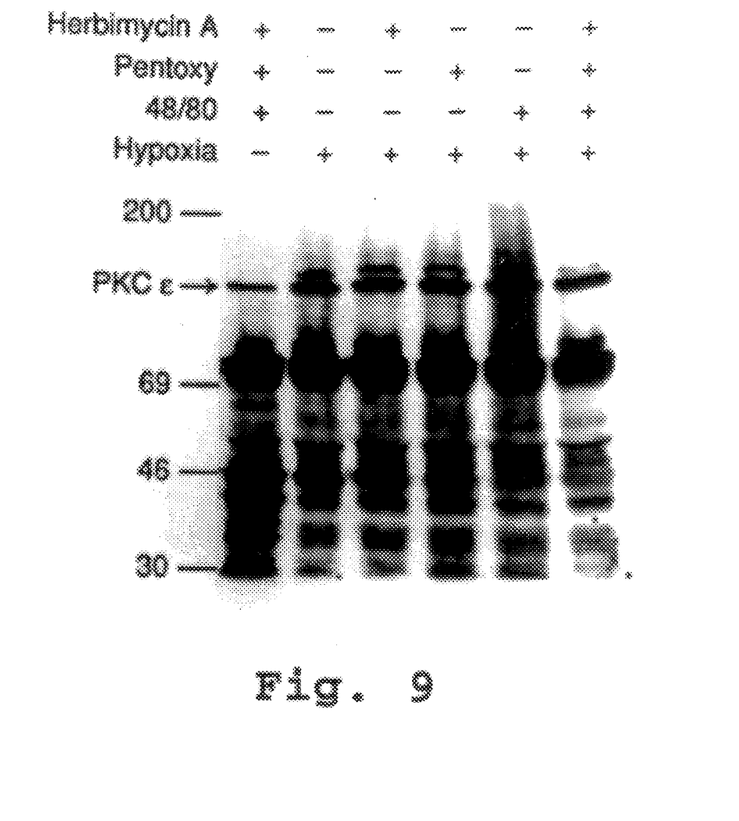
FIG. 9 shows Western blots showing the effects of phospholipase inhibitors 40/80 and pentoxyfylline or in combination on PKC induction by hypoxia and TPA.

FIG. 9 is a Western blot showing the effect of the phospholipase inhibitor compounds 48/80 and pentoxyfylline on PKC epsilon induction by hypoxia and TPA. Compound 48/80 and pentoxyfylline alone or in combination do not inhibit PKC activation by TPA during hypoxia. In addition, the tyrosine kinase inhibitor herbimycin A has no effect on PKC induction when used alone or in combination with the two phospholipase inhibitors. Therefore, compound 48/80 and pentoxyfylline are not protecting the cell from TPA mediated cell killing by inhibiting PKC activation. Instead, these results suggest that activation of PKC results in activation of phospholipases that are involved in increasing cellular lethality selectively in hypoxic cells.

The following examples are intended to illustrate various aspects of tumor cell behavior under hypoxic conditions. The examples are in no way intended to limit the scope of the invention.

EXAMPLE 1

Effect of Drug Treatment on Hypoxic Tumor Cells

A. Cells Lines and Hypoxia Treatment

A549 human adenocarcinoma cells were maintained in culture with alpha MEM containing 10% fetal calf serum. Cells were plated two days before hypoxia treatment in 60 mm glass (Corning) tissue culture dishes with notched sides at a density of 1×106 cells/dish. Hypoxia treatment of cells may be performed in any method known and available to those skilled in the art. Preferably, the method described in Giaccia, 1992a, herein incorporated by reference, is used.

On the day of the hypoxia treatment, cells were re-fed with fresh media and incubated 4–6 hours before being exposed to hypoxia. The petri dishes were preferably then placed in specially designed aluminum hypoxia chambers that are prewarmed overnight at 37° C. The chambers were sealed and subjected to successive rounds of evacuation followed by flushing with 95% $N_2$/5% CO2 while slowly being agitated on a reciprocating shaker. The chambers were then placed in a 37° C. incubator and kept on a reciprocating shaker for the duration of the hypoxic treatment.

One cycle of evacuation and flushing reduced the oxygen concentration in the media to 2.0%; three cycles result in an oxygen concentration of 0.2%; and five cycles result in an oxygen concentration of 0.02%. Oxygen concentration may be monitored with the use of a Clark-type electrode, such as commercially available from Controls Katharobic, Edmonton, Canada.

After hypoxic treatment, the seals to the chambers were broken, and the cells were washed with phosphate buffered saline, trypsinized, and then plated into tissue culture dishes to assay for colony forming ability.

B. Drug Treatment

All drugs were made from fresh stocks on the day of the treatment. In the combined drug and hypoxia treatments, the cells were pretreated for one hour with the drug before being exposed to hypoxia and then plated into tissue culture plates. Cells were then treated in accordance with several different methods: 1) exposure of the cells to thapsigargin for one hour prior to and continuous exposure for the duration of the hypoxia, and then plated for survival; 2) one hour exposure to the PKC activator drug in standard air followed by continuous exposure for the duration of hypoxia, and then plated for survival; 3) continuous exposure during hypoxia to TPA followed by immediate plating for survival; 4) 19 hour hypoxia treatment followed by one hour exposure to TPA in air or hypoxia using a Bactron II anaerobic chamber (Sheldon Labs, Cornelius, Oreg.), and then plating for survival; 5) continuous exposure during 19 hours of hypoxia with phospholipase inhibitors (compound 48/80 and pentoxyfylline), exposure to TPA for 1 hour in air, and then plating for survival.

The following drug concentrations may be used which, by themselves, cause little or no aerobic cytotoxicity and are close to the IC50 for enzyme activation: 12-O-tetradecanoyl-phorbol-13-acetate (TPA, 1 uM); 4α-phorbol-12-13-didecanoate (PDA, 1 uM); 2-acetyl-1-oleoylglycerol (OAG, 200 uM); thapsigargin (2 uM); compound 48/80 (50 mg/ml); and pentoxyfylline (1 mM). TPA, PDA, staurosporine, compound 48/80, and pentoxyfylline are commercially available from Sigma Chemicals, St. Louis, Mo. Thapsigargin, herbimycin A, and genistein are commercially available from Gibco/BRL, Gaithersberg, Md. OAG is commercially available from Fluka Chemicals, Ronkonkoma, N.Y. H7 and A23187 are commercially available from Calbiochem, San Diego, Calif.

C. Survival Assay

After various experimental treatments, cells were plated into Nunc tissue culture plates at the appropriate concentrations in triplicate. The plates are placed in a 37° C. incubator and stained 10 days after the experiment with 1% crystal violet in 10% methanol. Viable colonies are defined as colonies with 50 or more cells. FIG. 4 shows results from pooled data from at least two independent experiments.

EXAMPLE 2

Mechanism of Cell Necrosis

A. Pulsed Field Gel Electrophoresis.

Pulsed-field gel electrophoresis may be performed in any manner known and available to those skilled in the art. One preferred method is described in Giaccia, 1992b, which is incorporated herein by reference. Briefly, fresh media was added to all of the treatment groups on the day of the treatment. After treatment, cells were washed with phosphate buffered saline (PBS), trypsinized, and resuspended in 1% agarose/PBS. The cells embedded in agarose were allowed to solidify in glass tubes and then cut into 5 mm plugs. The plugs were lysed in 0.5M EDTA, 1% sarkosyl, and 1 mg/ml proteinase K (Boehringer Mannheim, Indianapolis), and incubated at 50° C. for 16 hours in this lysis buffer.

After dialyzing the plugs against 25 volumes of 10 mM Tris and 1 mM EDTA for 4 hours, the plugs were then treated with 20 mg/ml RNase A for 3 hours at 37° C. Pulsed-field gels preferably were run for 48 hours (15 min. at +1.25 V/cm and 1 min. in the reverse field at −5.0 V/cm).

B. Western Blot Analysis

Cells were lysed in a 50 mM phosphate buffer, sonicated with 4.5 second pulses of 75 W with cooling on ice between pulses, and followed by 3 rounds of freezing/thawing. Protein concentrations of each sample may be estimated using the bicinchoninic acid method. 200 µg of protein were loaded per lane. After running for 2 hours at 40 mA in a 7.5% polyacrylamide gel, the gel is transferred onto Hybond ECL, (Amersham, Arlington Heights, Ill.) for 2 hours with the use of a Bio-Rad semi-dry transfer system. After the transfer, the gel may be stained with 0.15% Coomassie blue to ensure uniform transfer. The membrane is probed with a PKC-epsilon antibody (Gibco/BRL) using method known and available to those skilled in the art. Preferably, the membrane is probed using the method described in Kim, et al., which is incorporated herein by reference, and autoradiographed utilizing enhanced chemiluminescence (ECL) according to the manufacturer's protocol (Amersham, Arlington Heights, Ill.).

EXAMPLE 3

Preparation of Collagen Vaso-occlusive Agent

The collagen suspension used in forming the cross-linked vaso-occlusive material of the invention is prepared from an aqueous solution of atelopeptide collagen, such as that described in U.S. Pat. No. 4,140,537, and incorporated herein by reference. The collagen is preferably derived from a cutaneous mammalian source, such as bovine or porcine corium.

A collagen fiber suspension is formed by reconstituting and neutralizing a collagen fibril solution, formed in accordance with the methods described in U.S. Pat. No. 4,140,537, above. The material is mechanically screened by repeated passage through a 60 mesh wire screen.

Cross-linking of the collagen is effected by glutaraldehyde treatment as follows. To a collagen solution having a concentration of about 3 mg/ml is added sufficient glutaraldehyde (pH 3) to obtain a final concentration of 0.0075%. After a reaction period of 16 hours, the cross-linked collagen is washed three times with approximately 100 volumes of neutral buffer (0.02M $Na_2PO_4$, 0.13M NaCl, pH 7.4). Each wash suspension is centrifuged at 17,000×g for about 5–10 minutes, the supernatant removed, and fresh solution added. The material is resuspended to a final concentration of about 30 mg/ml collagen, in 0.9% NaCl, 25 mM phosphate, pH 7.2.

EXAMPLE 4

Protein kinase C (PKC) activation Assay

Protein kinase C activation is measured in an assay that measures PKC phosphorylation activity using as substrate for PKC myelin basic protein. This assay is described in a reference by Ogita, et al., which is incorporated herein by reference. PKC activity is also measured by the method described by Farrar, et al. described as follows: PKC activity is measured at 36° in a reaction mixture of 20 mM Tris-Cl (pH 7.5), 20 mM $MgCl_2$, 1 mM $CaCl_2$, 20 µM or 120 µM [$\gamma^{32}P$]ATP (5,000–10,000 cpm/pmole), 50–140 µM acetylated $MBP_{4-14}$ (N-terminal acetylation) peptide (BRL Labs, Bethesda, Md.), 0.4 mg/ml histone III (Sigma, St. Louis, Mo.), 0.8 mM dithiothreitol, 80 µg/ml phosphatidyl serine and 1–5 µg/ml diolein in a 50 µl volume. The reaction was initiated by an appropriate amount of crude cytosol extract. The phosphorylated product from 10 µl of reaction mixture was quantified using phospho-cellulose paper and washing method of Cook, et al. Background $^{32}P$ incorporation in the absence of calcium and phosphatidyl serine/diolein and in the presence of 1 mM EGTA was subtracted from total incorporation in the complete PKC assay reaction mixture to determine the extent of PKC-dependent phosphorylation.

Suitable for use in this assay as a PKC source is either a crude extract, prepared as below, or, more preferably, purified PKC. Purified PKC is obtained from commercial sources.

Preparation of PKC extract from rat hippocampus. Hippocampi are removed from rat brains and homogenized in 5 volumes of ice-cold buffer A (20 mM Hepes, pH 7.5), 2 mM EGTA, 1 mM dithiothreitol, 10% glycerol, 50 µg/ml soybean trypsin inhibitor, 5 µg/ml aprotinin, 7 µM pepstatin A, 10 µM leupeptin, (1 mM phenylmethylsulfonyl fluoride), using a microcentrifuge tube pestle. All further procedures are carried out at 4° C. The homogenate is centrifuged at 710×g for 10 min. The supernatant is saved and the pellet re-homogenize in an additional 5 volumes of buffer A and centrifuged again as before. The two supernatants are combined and centrifuged at 100,000×g (Beckman TL-100 ultracentrifuge) for 20 minutes. The resulting supernatant fraction is diluted with buffer A to reach the desired protein concentration, for use as a crude source of PKC.

PKC may be partially purified from the above supernatant fraction by applying the supernatant to a 1 ml DEAE-cellulose column equilibrated with buffer A. After washing the column with 4 ml of buffer A, PKC is eluted with buffer A containing 0.1M NaCL to yield a partially purified PKC fraction.

Although the invention has been described with respect to particular compositions and treatment methods, it will be appreciated that various changes and modifications can be made without departing from the invention.

It is claimed:

1. A method of selectively killing cells in a solid tumor in a subject comprising administering to the subject, a compound effective to activate protein kinase C activity in the cells of the tumor, via a route effective to direct the compound to hypoxic cells in the tumor, where said compound is selected from the group consisting of a phorbol ester protein kinase C activator, a diacylglycerol activator of protein kinase C, and thapsigargin, and by said administering, achieving a substantially higher degree of cytotoxicity in such hypoxic cells than in normally oxygenated cells.

2. The method of claim 1, wherein said administering is by intravenous delivery of compound.

3. The method of claim 1, wherein the tumor contains hypoxic cells by virtue of poor vascularization of the tumor, said method further comprising identifying regions within the tumor containing said hypoxic cells, and where said administering includes introducing said compound directly into said hypoxic cell regions.

4. The method of claim 3, wherein said introducing is by hypodermic injection directly into said hypoxic cell regions.

5. The method of claim 3, wherein said introducing is by catheter delivery into vessels supplying said hypoxic cell regions.

6. The method of claim 1, which further comprises occluding vessels supplying blood to the tumor, to induce a hypoxic state in cells of the tumor.

7. The method of claim 6, wherein said occluding includes delivering a vasoconstrictive agent to the tumor site, prior to or at the time of said administering.

8. The method of claim 6, wherein said occluding includes delivering a vaso-occlusive agent to the tumor site, via catheter administration, prior to or at the time of said administering.

9. The method of claim 8, wherein said vaso-occlusive agent contains said compound in releasable form.

10. The method of claim 1, wherein said compound is 12-O-tetradecanoylphorbol-13-acetate or phorbol 12,13-dibutyrate.

11. The method of claim 1, wherein said compound is 2-acetyl-1-oleylglycerol.

12. The method of claim 1, wherein said compound is thapsigargin.

13. A vaso-occlusion composition for use in treating a solid tumor, by catheter delivery of the composition to vessels feeding the tumor, comprising a vaso-occlusion agent effective to form a stable vaso-occlusive mass when injected from a catheter into a vessel, to occlude blood flow in the vessel, and contained in said agent, in a releasable form, a compound effective to activate protein kinase C activity in mammalian tumor cells, where said compound is selected from the group consisting of a phorbol ester protein kinase C activator, a diacylglycerol activator of protein kinase C, and thapsigargin.

14. The composition of claim 13, wherein said vaso-occlusive agent is composed of collagen.

15. The composition of claim 13, wherein said compound is 12-O-tetradecanoylphorbol-13-acetate or phorbol 12,13-dibutyrate.

16. The composition of claim 13, wherein said compound is 2-acetyl-1-oleylglycerol.

17. A method of selectively killing cells in a solid tumor in a subject comprising:

administering to the subject, a compound effective to activate protein kinase C activity in the cells of the tumor, via a route effective to direct the compound to hypoxic cells in the tumor;

transforming cells in the tumor with a vector containing (i) a gene encoding a yeast oxygen-dependent repressor protein, a promoter upstream of the gene effective to ensure high levels of transcription of the gene, and (ii) an oxygen-dependent repressor sequence, and under the control of this sequence, a minimal promoter and a gene encoding tumor necrosis factor protein, and by said administering, achieving a substantially higher degree of cytotoxicity in such hypoxic cells than in normally oxygenated cells.

18. The method of claim 17, wherein said vector further includes a protein kinase C responsive element upstream of said oxygen-dependent repressor.

* * * * *